US00PP26321P2

(12) United States Plant Patent
Smith

(10) Patent No.: US PP26,321 P2
(45) Date of Patent: Jan. 19, 2016

(54) ***CHRYSANTHEMUM* PLANT NAMED 'CIFZ0014'**

(50) Latin Name: *Chrysanthemum×morifolium*
Varietal Denomination: CIFZ0014

(71) Applicant: Syngenta Crop Protection AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 74 days.

(21) Appl. No.: 13/998,246

(22) Filed: Oct. 15, 2013

(51) Int. Cl.
*A01H 5/00* (2006.01)

(52) U.S. Cl.
USPC ..... Plt./292

(58) Field of Classification Search
USPC ..... Plt./284, 292
See application file for complete search history.

(56) References Cited

PUBLICATIONS

Plant Varieties Journal, Apr. 2013/No. 87.*

* cited by examiner

*Primary Examiner* — Keith Robinson
(74) *Attorney, Agent, or Firm* — Joshua L. Price

(57) ABSTRACT

A new *Chrysanthemum* plant named 'CIFZ0014' particularly distinguished by the medium sized purple decorative inflorescences with long peduncles, medium sized plant habit that is rounded and mounded in natural season, is more upright under blackcloth conditions, and a natural season response of Mid-September.

1 Drawing Sheet

Latin name of the genus and species of the plant claimed: *Chrysanthemum×morifolium.*

Varietal denomination: 'CIFZ0014'.

BACKGROUND OF THE NEW PLANT

The present invention comprises a new *Chrysanthemum*, botanically known as *Chrysanthemum×morifolium,* and hereinafter referred to by the variety name 'CIFZ0014'.

'CIFZ0014' is a product of a planned breeding program. The new cultivar has medium sized purple decorative inflorescences with long peduncles, medium sized plant habit that is rounded and mounded in natural season, is more upright under blackcloth conditions, and a natural season response of Mid-September.

'CIFZ0014' originated from a hybridization made in November 2008 in a greenhouse in Tenjo, Columbia. The female parent was a commercially available plant designated 'Zanmufive' , U.S. Plant Pat. No. 19,791, with red colored inflorescences, shorter plant size under blackcloth, with a natural season flowering response that is one week faster and a blackcloth response that is about five days faster than that of 'CIFZ0014'.

The male parent of 'CIFZ0014' was the unpatented, commercially available plant designated as 'Braque' with light lavender inflorescence color, smaller plant size and a natural season and blackcloth response that is about 10 days slower than that of 'CIFZ0014'. The resultant seed was sown and grown in a greenhouse in October 2010 in Gilroy, Calif. USA.

'CIFZ0014' was selected as one flowering plant within the progeny of the stated cross in February 2011 in Gilroy, Calif.

The first act of asexual reproduction of 'CIFZ0014' was accomplished when vegetative cuttings were propagated from the initial selection in April 2011 in a greenhouse in Gilroy, Calif.

BRIEF SUMMARY OF INVENTION

Horticultural examination of plants grown from cuttings of the plant initiated in April 2011, and continuing thereafter, has demonstrated that the combination of characteristics as herein disclosed for 'CIFZ0014' are firmly fixed and are retained through successive generations of asexual reproduction.

'CIFZ0014' has not been observed under all possible environmental conditions. The phenotype may vary significantly with variations in environment such as temperature, light intensity, and day length.

A Plant Breeder's Right for this cultivar was applied for in Canada on Mar. 8, 2013, No. 13-7955. 'CIFZ0014' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0014' with colors being as true as possible with an illustration of this type.

Figure 1:
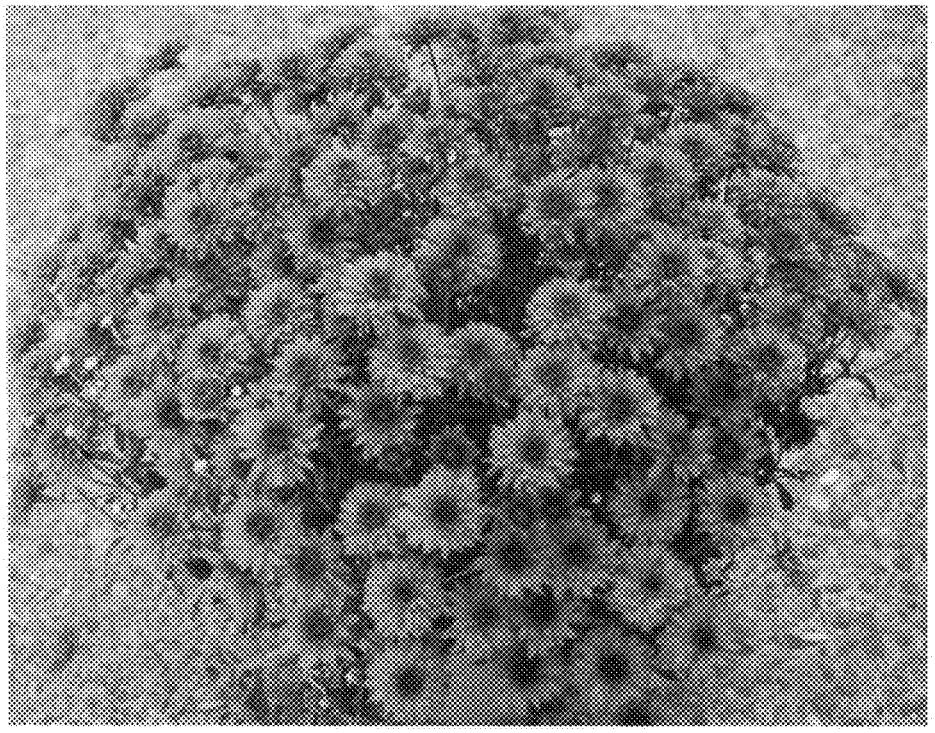
Figure 2:
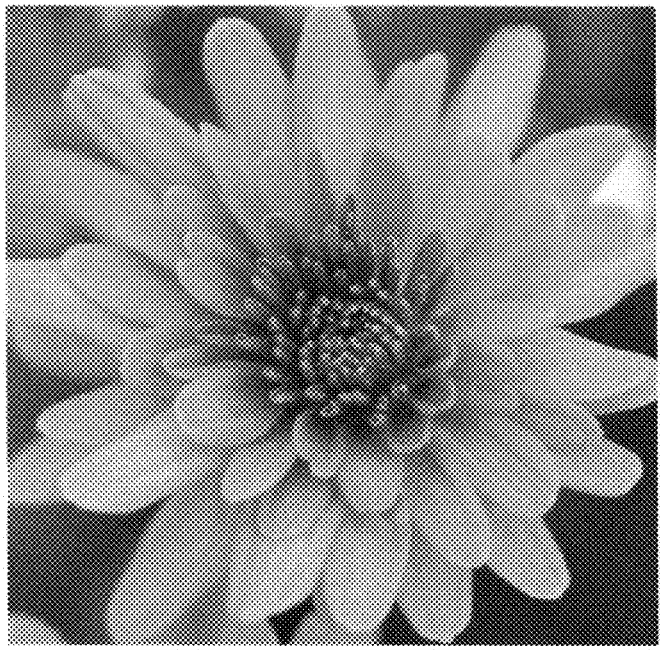

The photographic drawings show in FIG. 1 a flowering plant of the new variety and in FIG. 2 a close-up of the inflorescences.

DETAILED BOTANICAL DESCRIPTION

The plant descriptions, measurements and aforementioned photographs were taken in Gilroy, Calif. in August under natural light from plants that were about 11 weeks old. These plants were grown in 6 inch pots in a greenhouse trial under blackcloth conditions. These plants were not pinched.

Color references are made to The Royal Horticultural Society Colour Chart (R.H.S.) 2001.

TABLE 1

DIFFERENCES BETWEEN THE NEW VARIETY 'CIFZ0014' AND A MOST SIMILAR VARIETY

| | 'CIFZ0014' | 'Barbara' (U.S. Pat. No. PP8607) |
|---|---|---|
| Inflorescence size: | Larger | Smaller |
| Inflorescence color: | Darker | Lighter |
| Habit under blackcloth: | Less upright | More upright |
| Flowering habit: | More uniformly | Less uniformly |

Plant:

*Form, growth and habit.*—Herbaceous garden-type, stems upright and somewhat outwardly spreading, freely branching.

*Growth rate.*—Medium to vigorous.

*Plant height.*—20-22.0 cm.

*Plant height (inflorescence included).*—27-29.0 cm.

*Plant width.*—About 40-45.0 cm.

Roots:

*Number of days to initiate roots.*—About 4-6 days at about 22 degrees C.

*Number of days to produce a rooted cutting.*—About 14-16 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 147A.

*Immature, leaf color, lower surface.*—Closest to RHS 147B.

*Mature, leaf color, upper surface.*—Closest to RHS 147A.

*Mature, leaf color, lower surface.*—Closest to RHS 147B.

*Glossiness, upper surface.*—Weak.

*Length.*—3-3.7 cm.

*Width.*—2.5-2.9 cm.

*Shape.*—Short ovate.

*Base shape.*—Attenuate.

*Apex shape.*—Acute.

*Margin.*—Slightly palmately lobed; slightly dentate.

*Texture, upper surface.*—Bifid T-shaped hairs.

*Texture, lower surface.*—Bifid T-shaped hairs.

*Color of veins, upper surface.*—Indistinct.

*Color of veins, lower surface.*—Indistinct.

*Pattern of veining.*—Palmate.

*Petiole color.*—RHS 144B.

*Petiole attitude.*—Very strongly upwards.

*Length.*—0.7-0.9 cm.

*Diameter.*—0.2 cm.

*Texture.*—Bifid T-shaped hairs.

Stem:

*Quantity of main branches per plant.*—8-10.

*Color of stem.*—Closest to RHS 137A but appears lighter due to the hairs.

*Length of stem.*—10-12.0 cm.

*Diameter.*—0.3 cm.

*Length of internodes.*—0.5-0.7 cm.

*Texture.*—Bifid T-shaped hairs.

*Color of peduncle.*—Closest RHS 137A.

*Length of peduncle.*—7-8.0 cm.

*Aspect of peduncle.*—Upright.

*Peduncle diameter.*—0.15 cm.

*Texture.*—Bifid T-shaped hairs.

Inflorescence: Compositae, solitary decorative-type, inflorescences borne terminally above foliage, ray florets arranged acropetally on a capitulum.

*Quantity of short days to flowering (response time).*—7 weeks.

*Natural season flowering.*—Mid-September.

*Quantity of inflorescences per plant.*—165-180; with several more in immature stages.

*Lastingness of individual blooms on the plant.*—About 6 weeks from the first color depending on conditions.

*Corolla tube.*—Small, hidden within flower cluster.

*Fragrance.*—Slightly spicy.

Bud (just when opening/showing color):

*Color.*—RHS 71A.

*Length.*—0.7-1.1 cm.

*Width.*—0.8-0.9 cm.

*Shape.*—Oblate.

Immature inflorescence:

*Diameter.*—3.0-3.6 cm.

*Color of ray florets, upper surface.*—RHS 71A.

*Color of ray florets, lower surface.*—RHS 187D but more grey.

Mature inflorescence:

*Diameter.*—4-4.3 cm.

*Depth.*—1.3-1.4 cm.

*Total diameter of disc.*—No disc showing.

*Receptacle color.*—RHS 145B.

*Receptacle height.*—0.2 cm.

*Receptacle diameter.*—0.1 cm.

Ray florets:

*Average quantity of florets.*—About 150 in several whorls.

*Color of florets, upper surface.*—RHS 61A but lighter.

*Color of florets, lower surface.*—RHS N74D.

*Length.*—1.8-1.9 cm.

*Width.*—0.4-0.6 cm.

*Shape.*—Elliptical.

*Orientation.*—Horizontal, once open.

*Apex shape.*—Rounded with a few praemorse.

*Base shape.*—Attenuate.

*Margin.*—Entire.

*Texture, upper surface.*—Papillose.

*Texture, lower surface.*—Papillose.

Disc florets:

*Average quantity of florets.*—About 6-8.

*Color of florets.*—RHS 158C base with RHS 1B apex.

*Length.*—0.175 cm.

*Width.*—0.1 cm.

*Shape.*—Tubular, elongated.

*Apex shape.*—Acute, 5 pointed.

*Texture, inner surface.*—Glabrous.

*Texture, outer surface.*—Glabrous.

Phyllaries:

*Quantity.*—15-20.

*Color, upper surface.*—RHS 137B to RHS 137C.

*Color, lower surface.*—RHS 137A.

*Length.*—0.4-0.5 cm.

*Width.*—0.1 cm.

*Shape.*—Lanceolate.

*Apex shape*.—Acute.
*Base*.—Cuneate.
*Margins*.—Entire.
*Texture, upper surface*.—Glabrous.
*Texture, lower surface*.—Bifid T-shaped hairs.

Reproductive organs:

*Pistil*.—1, found on both types of florets.
*Length*.—0.3 cm.
*Style color*.—RHS 1C but more green and translucent.
*Style length*.—0.2 cm.
*Stigma color*.—RHS 3A.
*Stigma shape*.—Bi-parted.
*Ovary color*.—RHS 155C.
*Ovary length*.—0.1 cm.
*Ovary width*.—0.05 cm.
*Stamens*.—4, found on only on the disc florets.
*Color of filaments*.—Closest to RHS 159C, but most all appear to be very undeveloped.
*Length filaments*.—0.1 cm.
*Anther color*.—No anthers found.
*Fertility/seed set*.—Has not been observed.
*Disease/pest resistance*.—Has not been observed.

What is claimed is:

1. A new and distinct variety of *Chrysanthemum* plant named 'CIFZ0014' substantially as illustrated and described herein.

* * * * *